United States Patent [19]

Kummer et al.

[11] 4,259,520

[45] Mar. 31, 1981

[54] PREPARATION OF BUTANEDICARBOXYLIC ACID ESTERS

[75] Inventors: Rudolf Kummer, Frankenthal; Heinz-Walter Schneider, Ludwigshafen; Franz-Josef Weiss, Weinheim, all of Fed. Rep. of Germany

[73] Assignee: BASF Aktiengesellschaft, Fed. Rep. of Germany

[21] Appl. No.: 2,329

[22] Filed: Jan. 10, 1979

[51] Int. Cl.$^3$ ............................................. C07C 67/38
[52] U.S. Cl. .................................................. 560/204
[58] Field of Search ........................................ 560/204

[56] References Cited

FOREIGN PATENT DOCUMENTS

| | | |
|---|---|---|
| 1518216 | 12/1970 | Fed. Rep. of Germany . |
| 1618156 | 2/1971 | Fed. Rep. of Germany ............ 560/206 |
| 2037782 | 2/1972 | Fed. Rep. of Germany . |
| 2630086 | 1/1978 | Fed. Rep. of Germany ............ 560/206 |
| 49-20177 | 5/1974 | Japan ........................................ 560/204 |

OTHER PUBLICATIONS

Matsuda, Bull. of Chem. Soc. Japan, 46, pp. 524-530 (1973).

*Primary Examiner*—Jane S. Myers
*Attorney, Agent, or Firm*—Keil & Witherspoon

[57] ABSTRACT

In a process for the preparation of butanedicarboxylic acid esters by
(a) reacting butadiene or hydrocarbon mixtures containing butadiene with carbon monoxide and a $C_1$–$C_4$-alkanol in the presence of a tertiary nitrogen base and a cobalt carbonyl catalyst at from 80° to 150° C. under superatmospheric pressure,
(b) removing the greater part of the tertiary nitrogen base together with any excess hydrocarbon and
(c) reacting the resulting pentenoic acid ester, in the presence of the catalyst remaining in the reaction mixture, and in the presence of the remaining amount of tertiary nitrogen base, with carbon monoxide and a $C_1$- to $C_4$-alkanol at from 140° to 200° C. under superatmospheric pressure, to give the butanedicarboxylic acid ester, the improvement wherein the reaction mixture in stage c) is substantially free from dissolved butadiene or butadiene bonded to the catalyst.

Butanedicarboxylic acid esters may be used for the preparation of polymers.

3 Claims, No Drawings

PREPARATION OF BUTANEDICARBOXYLIC ACID ESTERS

The present invention relates to a process for the preparation of butanedicarboxylic acid esters by reacting butadiene, or a hydrocarbon mixture containing butadiene, with carbon monoxide and an alkanol in the presence of a cobalt carbonyl catalyst and a tertiary nitrogen base.

German Laid-Open Application DOS No. 2,037,782 discloses a process for the preparation of adipic acid wherein butadiene is reacted with carbon monoxide and water under superatmospheric pressure at an elevated temperature in the presence of a rhodium compound as the catalyst. The yields of dicarboxylic acids achieved with this process do not offer encouragement to carry out the process industrially. According to a different process, described in German Published Application DAS No. 1,518,216, butadiene is converted to dicarboxylic acids in the presence of cobalt carbonyl, pyridine and water, at 430 bar and 210° C. The yield achieved is from 50 to 70% of theory, based on butadiene. In addition, Bulletin of the Chemical Society of Japan, 46 (1973), 524–530 discloses that dimethyl adipate is obtained by reacting butadiene with carbon monoxide and methanol in the presence of cobalt carbonyl and pyridine and then carbonylating the resulting methyl pentenoate with the same catalyst, the temperature being raised to 200° C. in the second stage. However, the yields of dimethyl adipate are only from 47 to 51%.

It is an object of the present invention to increase the yield of butanedicarboxylic acids obtained by carbonylation of butadiene and in particular to improve the effectiveness of carbonylation of the pentenoic acid ester obtained as an intermediate.

We have found that this object is achieved by providing a process for the preparation of butanedicarboxylic acids by (a) reacting butadiene or hydrocarbon mixtures containing butadiene with carbon monoxide and a $C_1$–$C_4$-alkanol in the presence of a tertiary nitrogen base and a cobalt carbonyl catalyst at from 80° to 150° C. under superatmospheric pressure, (b) removing the greater part of the tertiary nitrogen base together with any excess hydrocarbon and (c) reacting the resulting pentenoic acid ester, without removing the catalyst and in the presence of the remaining amount of tertiary nitrogen base, with carbon monoxide and a $C_1$- to $C_4$-alkanol at from 140° to 200° C. under superatmospheric pressure, to give the butanedicarboxylic acid ester, wherein the reaction mixture in stage (c) is substantially free from dissolved butadiene or butadiene bonded to the catalyst.

The novel process has the advantage that it is possible to increase the yields of butanedicarboxylic acid esters without removing the catalyst, and in particular that it is possible to render more effective the stage wherein pentenoic acid esters are carbonylated to give butanedicarboxylic acid esters.

The starting material is pure 1,3-butadiene or a hydrocarbon mixture containing butadiene. Such hydrocarbon mixtures for example contain, in addition to butadiene, saturated hydrocarbons of 3 to 5 carbon atoms and mono-unsaturated olefins of 3 to 5 carbon atoms. The butadiene content should as a rule be more than 10% by weight. In industry, $C_4$-cuts, in particular, are used as the starting mixture. This definition embraces all mixtures of predominantly non-branched $C_4$-hydrocarbons which contain more than 10% by weight of 1,3-butadiene (butadiene) and more than 15% by weight of butenes. Depending on the origin of the mixture, the individual components are normally present in the following proportions in the mixtures:

butadiene 10–70, on average 40–60, % by weight
isobutene 15–40, on average 20–35, % by weight
but-1-ene 10–40, on average 10–25, % by weight
but-2-ene 5–20, on average 5–15, % by weight
butane 1–10, on average 1–10, % by weight
butynes 0.1–3, on average 0.1–3, % by weight Such $C_4$-cuts are obtained, for example, on dehydrogenation of butane or butene and as by-products for the production of ethylene by thermal cracking of naphtha or higher hydrocarbon cuts.

Suitable $C_1$–$C_4$-alkanols are methanol, ethanol, propanol, butanol and isobutanol. The use of methanol is particularly preferred. Advantageously, the alkanol is used in excess, especially in an amount of from 1.5 to 5 moles per mole of butadiene.

The reaction is preferably carried out at from 120° to 140° C. under pressures of from 600 to 1,200 bar. As a rule, from 0.01 to 0.1 gram atom of cobalt, in the form of a cobalt carbonyl complex, is used per mole of butadiene.

Carbon monoxide is advantageously employed in excess, for example in from 1.5 to 10 times the stoichiometrically required amount.

Suitable tertiary nitrogen bases advantageously have a $pK_a$ of from 3 to 11, with the proviso that they are preferably lower-boiling than the pentenoic acid ester to be prepared. Preferably, N-heterocyclic compounds, eg. pyridine ($pK_a$ 5.3), methylpyridines, eg. 3-picoline ($pK_a$ 6.0) and isoquinoline ($pK_a$ 5.4), and trialkylamines, eg. trimethylamine ($pK_a$ 11.0), are used. Pyridine is of particular importance industrially. It has proved especially advantageous to use from 20 to 50 moles of pyridine per mole of cobalt carbonyl catalyst.

The cobalt catalysts used in stage (a) are either produced in situ from cobalt salts, eg. salts of fatty acids, such as formates, acetates, propionates or butyrates, or, advantageously, are introduced as preformed cobalt carbonyl. In particular, it has proved advantageous to introduce the cobalt carbonyl catalyst into the reaction mixture as a solution in butadiene or a $C_4$-cut. Such a solution is obtained, for example, by reacting an aqueous solution of a cobalt salt of a fatty acid with a mixture of carbon monoxide and hydrogen in the presence of active charcoal at from 100° to 170° C. under a pressure of from 100 to 400 bar. The resulting cobalt carbonyl is then extracted from the aqueous solution by means of butadiene or a $C_4$-cut.

The reaction mixture obtained in stage (a) contains unconverted butadiene, with or without other hydrocarbons, tertiary nitrogen bases, cobalt carbonyl catalysts, unconverted alkanols, the pentenoic acid ester formed as the desired product, by-products, eg. esters of valeric acid, vinylcyclohexene, butenylketones and butylketones, and butadiene polymers.

It is an essential feature of the invention that in stage (c) the reaction mixture is substantially free from dissolved butadiene or butadiene bonded to the catalyst. Advantageously, at least 50%, more especially 80%, of the cobalt catalyst should, in stage (c), not be in the form of a $\pi$-allyl complex with butadiene. This can easily be checked in that, if conversion in stage (a) is incomplete, ie. butadiene is present, the IR spectrum of the catalyst is essentially characterized by the cobalt carbonyl bands at 2,010 and 2,080 cm$^{-1}$, whilst the band at 1,930 cm$^{-1}$ is less pronounced. As the butadiene content is progressively reduced, the bands at 2,010 and 2,080 cm$^{-1}$ disappear, whilst the carbonyl band at 1,930 cm$^{-1}$ becomes the main carbonyl band. This indicates that the cobalt carbonyl complex which contains bonded butadiene has been virtually completely converted to a pure cobalt carbonyl complex which only retains small amounts of bonded butadiene.

A suitable composition of catalyst, appropriate for stage (c), is obtained, for example, by converting, in stage (a), at least 99% by weight of the butadiene employed. Thereafter the pressure of the resulting reaction mixture is released and tertiary nitrogen bases contained in the mixture are very largely removed, as are any excess hydrocarbons. This removal is effected, for example, by distillation or other separation processes, eg. extraction. Advantageously, tertiary nitrogen bases and any excess hydrocarbon are removed by distillation under reduced pressure. Advantageously, the tertiary nitrogen bases are removed to the point where their content is only from 2 to 10 moles per mole of cobalt carbonyl catalyst.

Since it is frequently inappropriate to convert at least 99% of the butadiene, especially if a butadiene-containing hydrocarbon is used, a catalyst which is effective in stage (c) is in such cases obtained by removing the free butadiene from the reaction mixture obtained in stage (a), after releasing the pressure, by, for example, distillation, with or without other hydrocarbons which may be present. In removing this butadiene care is taken, however, that the entire amount of tertiary nitrogen base remains in the reaction mixture. The latter is then treated with carbon monoxide at from 100° to 160° C. under a pressure of from 50 to 200 bar. The treatment time is as a rule from 5 to 60 minutes. During this treatment the cobalt carbonyl catalyst is converted to a form appropriate for stage (c). Following this after-treatment, the greater part of the tertiary nitrogen bases contained in the reaction mixture is then removed as explained above, until the amount remaining is as stated above.

It is to be noted that during distillation the temperature in the bottom should not exceed 75° C., so as to avoid decomposition of the cobalt catalyst.

The pentenoic acid ester remaining in the reaction mixture thus obtained is reacted with carbon monoxide and a $C_1$-$C_4$-alkanol, if necessary after addition of an appropriate fresh amount of alkanol, at from 140° to 200° C. under a pressure of from 100 to 400 bar in the presence of the cobalt catalyst present in the reaction mixture and of the tertiary nitrogen base. As mentioned above, from 2 to 10 moles of tertiary nitrogen base are present in the reaction mixture per mole of cobalt catalyst. Advantageously, the reaction is carried out at from 150° to 180° C. under a pressure of from 100 to 400 bar. The amount of alkanol present is, for example, from 1.5 to 4 moles per mole of pentenoic acid ester. It has also proved advantageous to add a few percent by volume of hydrogen, eg. from 0.2 to 4% by volume, to the carbon monoxide, in order to increase the rate of reaction. After releasing the pressure, excess alkanol and free tertiary nitrogen base are distilled from the reaction mixture obtained. This does not remove the tertiary nitrogen bases bonded chemically to the catalyst (from 1 to 2 moles per gram atom of cobalt). To avoid decomposition of the cobalt complex, with undesirable formation of metallic cobalt, it has proved advantageous to pass a slow stream of carbon monoxide, or of a gas containing carbon monoxide, into the bottom of the column.

The reaction mixture which is left, and which contains catalyst, butanedicarboxylic acid ester and by-products, is treated with an oxidizing agent, eg. molecular oxygen or a gas containing the latter, eg. air, in an aqueous acid medium, advantageously at a pH of from 3 to 6, and advantageously at from 80° to 160° C. After the treatment, the mixture is separated into an organic phase and an aqueous phase, for example by decanting. Fractional distillation of the organic phase gives the residual tertiary nitrogen base, the unconverted pentenoic acid ester, which is recycled to the carbonylation reaction, and a mixture of butanedicarboxylic acid esters (80–85% by weight of adipic acid esters, 11–15% by weight of 2-methylglutaric acid esters and 3–6% by weight of 2-ethylsuccinic acid esters). The ester mixture can be used to prepare diols or polyesters. The adipic acid ester obtainable from the ester mixture by fractional distillation may be used for the preparation of adipic acid. The aqueous phase containing cobalt salts, with or without free acid, is advantageously recycled, being used as a starting solution for the preparation of the cobalt catalyst.

The adipic acid esters and/or adipic acid obtained according to the invention may be used for the preparation of polymers.

The Examples which follow illustrate the process of the invention.

EXAMPLE 1

(a) Per hour, 310 ml of a $C_4$-cut, which contains 43% by weight of butadiene (1.57 moles) and 3.7 g of cobalt in the form of cobalt carbonyl compounds are introduced into the bottom of a high-pressure vessel of 1.9 liters capacity. In addition, 124 g (1.57 moles) of pyridine, 100 g (3.14 moles) of methanol and 60 liters (S.T.P.) of carbon monoxide are introduced per hour. The carbonylation takes place at 140° C. and 600 bar. The product taken off at the top of the high-pressure vessel is let down, resulting in the removal, in the gaseous form, of excess $C_4$-hydrocarbons, in addition to excess carbon monoxide. The excess hydrocarbons contain virtually no butadiene so that, based on butadiene, the reaction is quantitative.

(b) Per hour, about 52 g of methanol and 100 g of pyridine as well as hydrocarbons are distilled from the material discharged, the distillation being carried out under reduced pressure so as not to damage the catalyst. The distillation bottom temperature is kept to a maximum of 65° C.

(c) The distillation residue thus obtained, which contains 3.7 g of cobalt as the carbonyl complex, 165 g (1.44 moles) of pentenoic acid esters and 22.8 g (0.228 mole) of pyridine is fed, together with 92 g (2.88 moles) of methanol and 55 liters (S.T.P.) of carbon monoxide, containing 2% by volume of hydrogen, continuously into the bottom of a further high-pressure vessel of 1.7 liters capacity. The carbonylation is carried out at 170° C. under a pressure of 150 bar. Gas-chromatographic analysis of the products discharged shows that 95% by weight of the methyl pentenoate employed has been converted, the selectivity in respect of dimethyl adipate being 76%.

COMPARATIVE EXAMPLE

The procedure described in Example 1 is followed, but in stage 1(a) the reaction is carried out at a lower temperature, viz. 120° C., the conversion achieved, based on butadiene, being only 80%, according to gas-chromatographic analysis. Thereafter the procedure followed is entirely as described in Example 1; the material discharged from stage (c) shows, according to gas-chromatographic analysis, a conversion of 56% by weight of the methyl pentenoate employed, the selectivity being 77% in respect of dimethyl adipate.

The lowering of the conversion of methyl pentenoate shows clearly that the catalyst has not been adequately converted into the active form for stage (c).

EXAMPLE 2

The procedure followed is as in Example 1, but the reaction is carried out at 130° C. and 600 bar, so that only 90% of the butadiene is converted. After releasing the pressure, the $C_4$-hydrocarbons and unconverted butadiene are separated off. The reaction product is then treated, in the presence of the entire pyridine and methanol, in a further high-pressure vessel of 0.4 liter capacity, for 60 minutes at 140° C. under a CO pressure of 100 bar. This results in over 95% conversion of the catalyst, which was previously quantitatively present in a chemically bonded form, as the $\pi$-allyl complex, into butadiene-free cobalt carbonyl.

(b) After letting down to atmospheric pressure, about 100 g of pyridine and 52 g of methanol are distilled off per hour, under reduced pressure (bottom temperature 65° C.).

(c) The distillation residue thus obtained, which contains the cobalt carbonyl catalyst, 165 g (1.44 moles) of pentenoic acid ester and 22.8 g (0.288 mole) of pyridine is fed, together with 92 g (2.88 moles) of methanol and 55 liters (S.T.P.) of carbon monoxide, continuously into the bottom of a further high-pressure vessel of 1.7 liters capacity. The carbonylation is carried out at 170° C. and 150 bar. Gas-chromatographic analysis of the products discharged shows that 98.5% of the methyl pentenoate employed has been converted, the selectivity in respect of dimethyl adipate being 77.5%.

We claim:

1. In the process for the preparation of butanedicarboxylic acid esters by
   (a) reacting butadiene or hydrocarbon mixtures containing butadiene with carbon monoxide and a $C_1$–$C_4$-alkanol in the presence of a tertiary nitrogen base and a cobalt carbonyl catalyst at from 80° to 150° C. under superatmospheric pressure,
   (b) removing the greater part of the tertiary nitrogen base together with any excess hydrocarbon from the reaction mixture and
   (c) reacting the resulting pentenoic acid ester, in the presence of the catalyst remaining in the reaction mixture, and in the presence of the remaining amount of tertiary nitrogen base, with carbon monoxide and a $C_1$- to $C_4$-alkanol at from 140° to 200° C. under superatmospheric pressure, to give the butane-dicarboxylic acid ester, the improvement wherein the catalyst is not separated from the reaction mixture during states (a) to (c), the reaction mixture in stage (c) is substantially free from the dissolved butadiene, and at least 80% of the cobalt catalyst is not in the form of a $\pi$-allyl complex with butadiene by maintaining the conversion in stage (a) of at least 99% of the butadiene in the reaction mixture or by treating the mixture remaining after the removal of the hydrocarbons in stage (b) with carbon monoxide under a pressure of from 50 to 200 bar at from 100° to 160° C. while maintaining a molar ratio of the cobalt catalyst to the tertiary nitrogen base of 1:20–50.

2. The process of claim 1, wherein from 20 to 50 moles of tertiary nitrogen base are used per mole of cobalt carbonyl catalyst in stage (a).

3. The process of claim 1, wherein from 2 to 10 moles of tertiary nitrogen base are used per mole of cobalt catalyst in stage (c).

* * * * *